(12) United States Patent
Röhrl

(10) Patent No.: US 7,201,743 B2
(45) Date of Patent: Apr. 10, 2007

(54) INCONTINENCE DIAPER FOR ADULTS (75) Inventor: Wolfgang Röhrl, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 29 days.

(21) Appl. No.: 10/528,786

(22) PCT Filed: Aug. 2, 2003

(86) PCT No.: PCT/EP03/08586

§ 371 (c)(1), (2), (4) Date: Mar. 23, 2005

(87) PCT Pub. No.: WO2004/032812

PCT Pub. Date: Apr. 22, 2004

(65) Prior Publication Data
US 2006/0036229 A1    Feb. 16, 2006

(30) Foreign Application Priority Data
Sep. 30, 2002    (DE) .................. 102 46 365

(51) Int. Cl.
A61F 13/56    (2006.01)

(52) U.S. Cl. .................. 604/390; 604/389

(58) Field of Classification Search .......... 604/379, 604/389, 390, 391, 383, 386
See application file for complete search history.

(56) References Cited

U.S. PATENT DOCUMENTS

| | | | | |
|---|---|---|---|---|
| 3,221,738 A | * | 12/1965 | Ekberg et al. | 604/366 |
| 3,776,232 A | * | 12/1973 | Schaar | 604/385.01 |
| 3,999,546 A | * | 12/1976 | Feldman et al. | 604/390 |
| 4,010,754 A | * | 3/1977 | Pieniak | 604/390 |
| 4,034,752 A | * | 7/1977 | Tritsch | 604/390 |
| 4,090,516 A | * | 5/1978 | Schaar | 604/390 |
| 4,209,016 A | * | 6/1980 | Schaar | 604/390 |
| 4,253,461 A | * | 3/1981 | Strickland et al. | 604/389 |
| 4,410,326 A | * | 10/1983 | Dussaud et al. | 604/390 |
| 4,500,316 A | | 2/1985 | Damico | |
| 4,578,072 A | * | 3/1986 | Lancaster | 604/385.24 |
| 4,704,115 A | | 11/1987 | Buell | |
| 4,726,971 A | * | 2/1988 | Pape et al. | 428/41.9 |
| 4,820,296 A | * | 4/1989 | Masliyah | 604/385.03 |

(Continued)

FOREIGN PATENT DOCUMENTS

EP    0 000 969    3/1979

(Continued)

Primary Examiner—Tatyana Zalukaeva
Assistant Examiner—Paula L. Craig
(74) Attorney, Agent, or Firm—Paul Vincent (57) ABSTRACT The invention relates to disposable incontinence diapers for adults. At least two closure means (24, 26) are provided on each respective side section (22, 24) or longitudinal edge section (18, 20) and are distanced from each other in a longitudinal direction (30) in order to adapt the diapers in a more effective manner to the actual requirements made thereof. The invention is characterized in that the respective closure means (26) which is located further away from the edge of the hip (16) and the impact section (34) associated therewith are configured in such a way that the adhesive connection, beginning with the closed state of the diapers, only becomes detached when the force is higher than that of the adhesive connection of the closure means (24) located nearer to the edge of the hip (16) and the impact section (32) associated therewith.

15 Claims, 4 Drawing Sheets

U.S. PATENT DOCUMENTS

| | | | |
|---|---|---|---|
| 4,850,988 A * | 7/1989 | Aledo et al. | 604/385.21 |
| 4,850,992 A * | 7/1989 | Amaral et al. | 604/389 |
| 4,861,635 A * | 8/1989 | Carpenter et al. | 428/41.3 |
| 4,995,873 A * | 2/1991 | Knight | 604/391 |
| 5,019,073 A * | 5/1991 | Roessler et al. | 604/391 |
| 5,242,436 A * | 9/1993 | Weil et al. | 604/385.29 |
| 5,370,634 A * | 12/1994 | Ando et al. | 604/385.21 |
| 5,386,595 A * | 2/1995 | Kuen et al. | 2/400 |
| 5,401,275 A * | 3/1995 | Flug et al. | 604/391 |
| 5,560,798 A | 10/1996 | Brusky | |
| 5,897,545 A * | 4/1999 | Kline et al. | 604/386 |
| 6,056,732 A | 5/2000 | Fujioka | |
| 6,102,901 A * | 8/2000 | Lord et al. | 604/386 |
| 6,120,866 A * | 9/2000 | Arakawa et al. | 428/40.1 |
| 6,191,055 B1 | 2/2001 | Boyer | |
| 6,307,120 B1 | 10/2001 | Glaug | |
| 6,365,793 B1 | 4/2002 | McLaughlin | |
| 6,402,730 B1 * | 6/2002 | Malowaniec | 604/389 |
| 6,454,751 B1 * | 9/2002 | Olson | 604/389 |
| 6,641,568 B2 * | 11/2003 | Ashton et al. | 604/385.01 |
| 6,663,612 B2 * | 12/2003 | Shingu et al. | 604/391 |
| 2003/0032933 A1 * | 2/2003 | Sayama | 604/386 |
| 2003/0100880 A1 * | 5/2003 | Magee et al. | 604/389 |
| 2004/0153046 A1 * | 8/2004 | Ito et al. | 604/391 |

FOREIGN PATENT DOCUMENTS

| | | |
|---|---|---|
| EP | 0 768 073 | 4/1997 |
| EP | 1 048 279 | 11/2000 |
| WO | WO 98/35642 | 8/1998 |
| WO | WO 00 35397 | 6/2000 |
| WO | WO 00/37005 | 6/2000 |
| WO | WO 00/74621 | 12/2000 |
| WO | WO 01/66057 | 9/2001 |

* cited by examiner

INCONTINENCE DIAPER FOR ADULTS

This application is the national stage of PCT/EP2003/008586 filed on Aug. 2, 2003 and also claims Paris Convention priority of DE 102 46 365.4 filed on Sep. 30, 2002.

BACKGROUND OF THE INVENTION

The invention concerns a disposable incontinence diaper for adults, comprising a front area, a rear area and a center area which is disposed in a longitudinal direction therebetween, and comes to rest in the crotch region of the user, and with mechanically or adhesively effective closing means which are disposed on side sections, in particular, on longitudinal edge sections of the rear area or the front area to adhesively interact with an impact section at the front area or rear area, wherein at least two closing means are provided on a respective side section or longitudinal edge section, which are separated from each other in the longitudinal direction.

A diaper of this type is described in EP 0 000 969 B1. U.S. Pat. No. 4,209,016 also discloses a diaper comprising closing means which are either separated or can be separated such that, in addition to the primary closing function provided by a tape strip disposed close to the hip edge, a second tape strip can be positioned below the first tape strip to exercise additional tensile forces for improved seating of the diaper on the body of the user.

WO 00/37005 also discloses an incontinence diaper of this type with at least three closing means on both sides.

It is the underlying purpose of the present invention to improve a disposable incontinence diaper of this type to enhance its adaptation to stresses in the closing area which occur during use.

SUMMARY OF THE INVENTION

This object is achieved in accordance with the invention in an incontinence diaper of this type in that the closing means which is further removed from the hip edge and the associated impact section are each designed such that, when the diaper is closed, the adhesive bond between them is released only by a force which is larger than the adhesive bond between the closing means and its impact section disposed closer to the hip edge.

Figure 1:
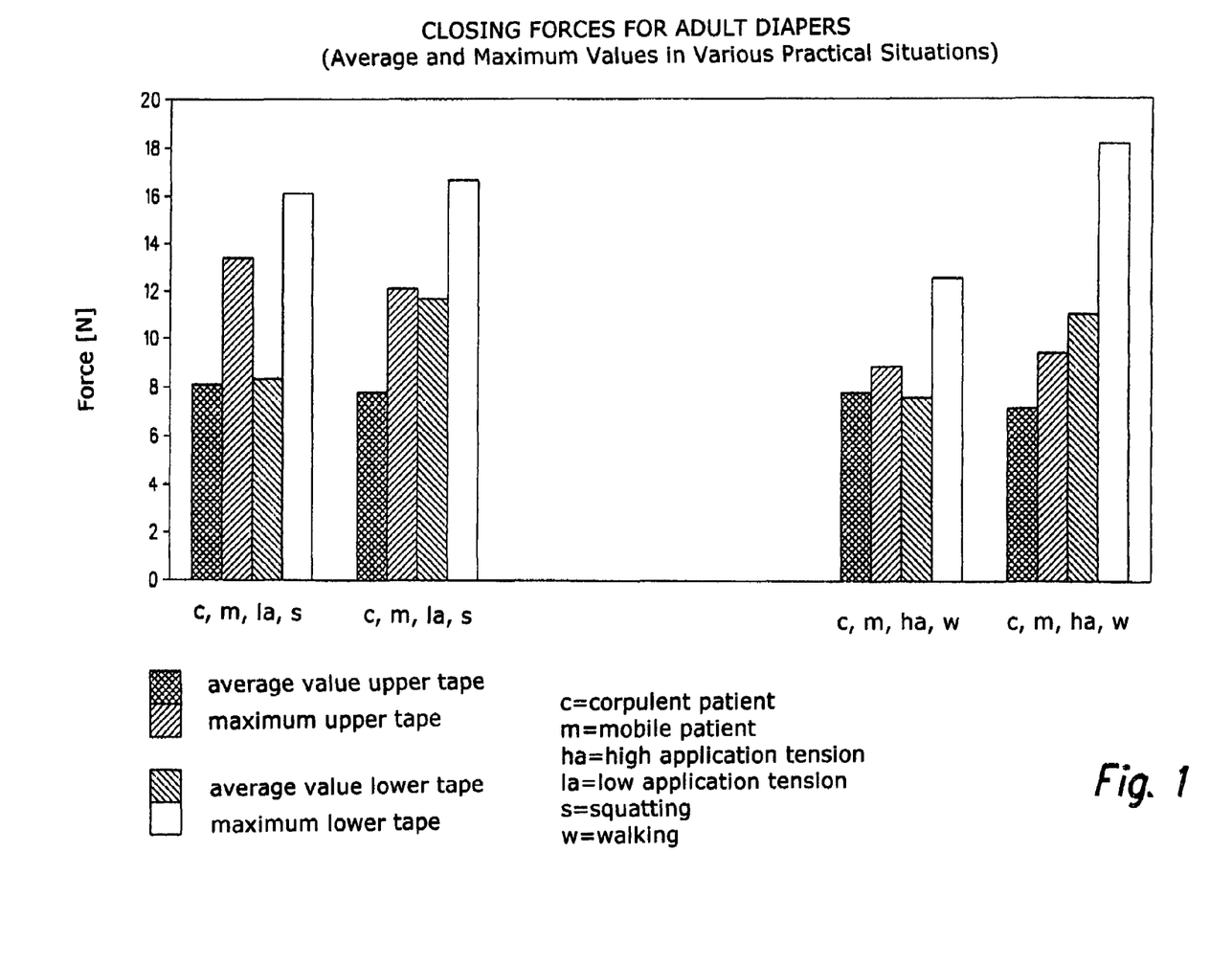
FIGS. 1 and 2 show forces determined under various conditions of wear which occur in the closing system of incontinence diapers.
Figure 2:
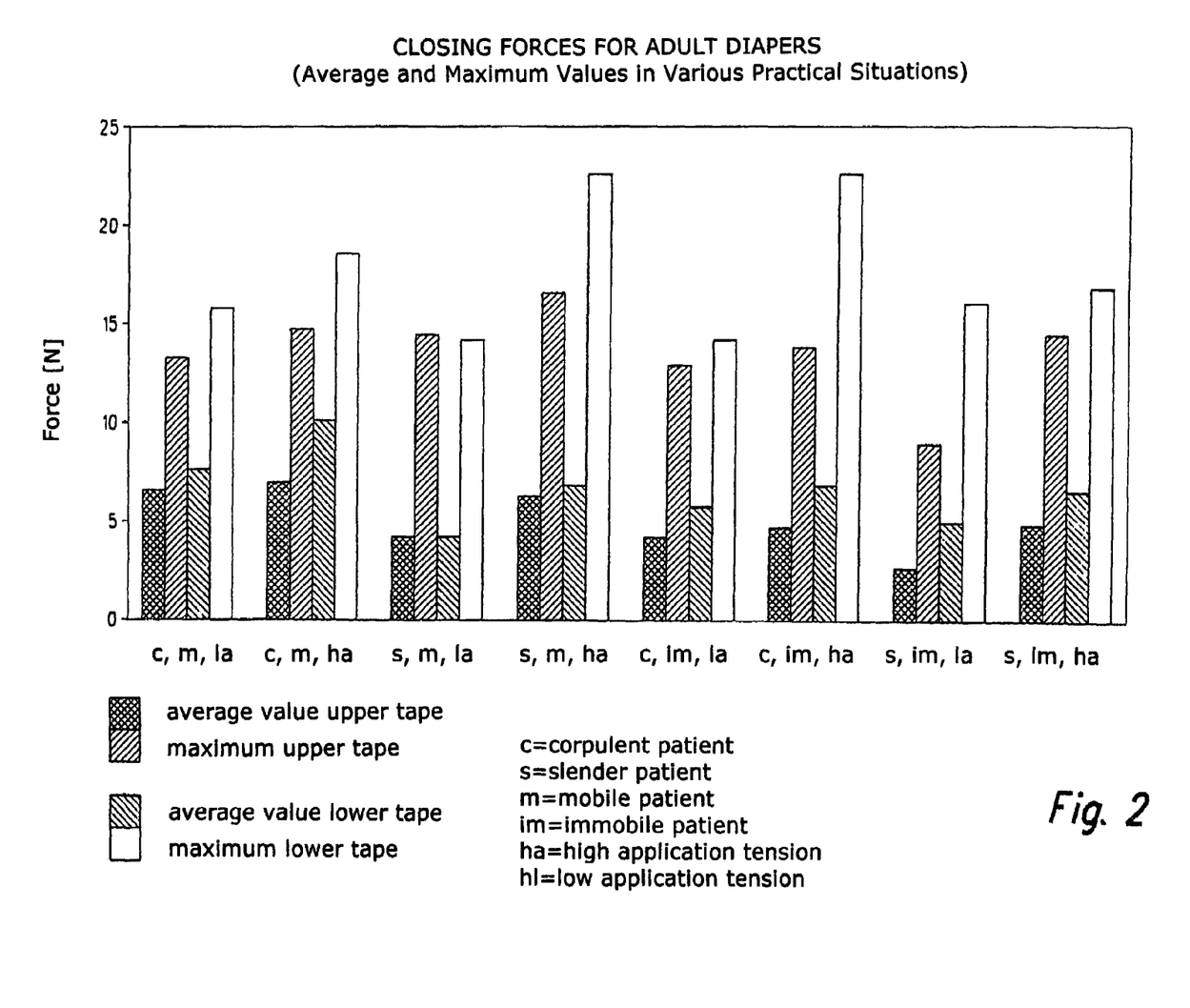

The present invention is based on the finding that, in particular with incontinence diapers for adults, i.e. for mobile and also immobile adults needing care, the stresses acting on the closing system further removed from the hip during actual wear are larger than those acting on the closing system close to the hip. These stresses are tensile forces acting in the direction of flat extension of the closing system. The applicant has discovered this surprising fact through extensive test measurements using strain measuring strips distant from and close to the hip, i.e. during wear, in the upper and lower closing systems of incontinence diapers. The results of such measurements are shown in FIGS. 1 and 2 and are described below.

Consideration of large stresses in the configuration of conventional incontinence diapers for adults has often resulted in overdimensioning of tapes, tabs, adhesive and/or mechanical closing means, leading to consumption of large amounts of raw material.

In contrast thereto and in accordance with the present invention, it has turned out to be sufficient to match the closing system of an incontinence diaper of this type to the maximum stresses in the area of the closing means disposed further removed from the hip, and to provide a weaker adhesive bond between the closing means and the corresponding impact section close to the hip. This permits economical and also ecologically optimized use of raw materials.

In general, the closing means, usually in the form of tapes or tabs, need not be particularly optimized to adopt stresses without being damaged. Conventional closing means are generally sufficiently stable and suitable to accept the tensile forces or tensile stresses which occur during wear. The main concern is the design of the adhesive bond between the closing means and the corresponding impact sections as claimed and mentioned above, since this adhesive bond could become detached in particular load situations. The inventive finding and the inventive suggested configuration of the closing system further improves incontinence diapers in view of the actual stresses occuring during wear, and also in view of optimizing consumption of raw materials.

A stronger adhesive bond in the region of the closing means disposed distant from the hip can be obtained, e.g. in that the closing means disposed distant from the hip have an adhesive area which has a larger active surface than those closer to the hip edge. If the closing means or the active adhesive area of the closing means and the associated impact areas are identical, i.e. the hook and loop material is the same or the adhesive closing tape material is the same, the larger surface of the active adhesive area of the closing means disposed further removed from the hip produces a stronger adhesive force than that of the closing means disposed close to the hip.

The larger surface of the active adhesive area of the closing means disposed further removed from the hip edge is thereby at least 1.2 times that, in particular 1.2 to 2 times that and preferably up to maximally 1.6 times or 1.5 times that of the active adhesive area of the closing means disposed closer to the hip edge.

In accordance with a preferred embodiment of the invention, the dimensions of the active adhesive area of the closing means disposed further removed from the hip edge is larger in the longitudinal direction of the diaper than the dimensions of the active adhesive area of the closing means disposed closer to the hip edge, as seen in this longitudinal direction. Closing tapes or tabs may be used to form the closing means distant from and close to the hip, or closing means having an adhesive or mechanically acting active bonding area of different dimensions in the longitudinal direction of the diaper may be used, wherein their dimensions in the transverse direction of the diaper may, in particular, be the same.

The impact section for the respective closing elements as mentioned above is to be understood in the broadest possible sense. It may be e.g. the back sheet foil of the incontinence diaper which forms an impact area for the closing means and must not be characterized in any particular manner. It is also feasible to form the respective impact section for the respective closing means by one single or several section(s) of a sheet material, e.g. a hook and loop material or a rather smooth material, to form an adhesive bond. The impact sections for the upper and lower closing means may, in particular, be formed on a respective side section of the diaper by one single, continuous impact section. In a corresponding manner, an impact section could extend from one side section to the other in a transverse direction which permits largely variable positioning of the respective closing means in a transverse direction to be able to adjust the incontinence diaper to the respective hip size of a user and to adjust the desired application tension.

In accordance with a further embodiment, the dimensions of the active bonding area of the respective closing means in the longitudinal direction of the diaper substantially correspond to the dimensions of this closing means in this direction. An adhesive closing tape could thereby be provided over the entire tape width (which extends in the longitudinal direction of the diaper if the tape extends e.g. in a transverse direction of the diaper) with an adhesive coating which extends over the entire width of the closing tape.

The dimensions of the entire closing means disposed further removed from the hip edge are larger in the longitudinal direction of the diaper than the dimensions of the closing means disposed closer to the hip edge, as viewed in this direction.

As mentioned above, in the transverse direction of the diaper, the dimensions of the active adhesive area of the closing means disposed further removed from the hip edge can correspond substantially to the transverse dimensions of the active adhesive area of the closing means disposed closer to the hip edge. To provide an optically pleasant appearance of the hygiene article, the overall dimensions of the respective closing means are preferably selected to be equal in the transverse direction of the diaper.

Preferred dimensions of the closing means can be extracted from the dependent claims.

In accordance with a preferred embodiment of the invention, the closing means and the associated impact areas are designed such that the releasing force at which the adhesive bond between the closing means disposed further removed from the hip edge and the associated impact section is at least 45N, wherein this releasing force is measured as a maximum shearing force in a removal test between the closing means and the impact section. The term shearing force thereby means that the closing means and the impact section are clamped in a test arrangement in a tensile testing device to be described below and are moved apart in a plane under a withdrawal angle of substantially 0° (to determine the peeling off force or peel force, the closing means would be removed at an angle of substantially 180° such that the closing means is gradually detached). In the present determination of the maximum shearing force, the closing means is detached suddenly when the required releasing force from the impact section as simulated by a test substrate, has been reached.

The above-mentioned releasing force for the closing means disposed further removed from the hip and the associated impact section is, in particular, maximally 105N and preferably between 55 N and 95 N.

The corresponding releasing force of the closing means disposed close to the hip—again measured as maximum shearing force—is preferably at least 38 N. A preferred upper limit is 60 N. The releasing force of a preferred embodiment is between 40N and 55N.

Further features, details and advantages of the invention can be extracted from the claims and the drawing and the following description of measurements of the stress forces of incontinence diapers and of the inventive incontinence diaper in the test set-up to determine the releasing force. The individual elements of the claims constitute aspects of the current invention independently of their dependencies on other claims.

DESCRIPTION OF THE PREFERRED EMBODIMENT

FIGS. 1 and 2 show the test results of tensile forces measured under various wear conditions of incontinence diapers for adults in the area of the closing means. The tests were carried out with two test persons. Large and heavy test persons were selected who were, however, also associated with different physiologies, i.e. rather corpulent or rather slim. Various wear conditions were simulated. Mobile patients with normal walking and squatting motions (FIG. 1) were simulated as exemplary motion conditions. A distinction was made between a high diaper application tension and a low diaper application tension which can be varied through tight or rigid closing of the diaper through corresponding positioning of the closing elements (FIG. 1 left- and right-hand side). The respective blocks in FIG. 1 show the average value and the maximum value of the measured force values (tensile forces) for the upper and lower tape-like closing means, respectively.

It is clear that in both the squatting and walking load situations, the forces measured in the upper closing means disposed close to the hip region are smaller than those in the lower closing means disposed further removed from the hip, for both high as well as low application tension.

The tensile forces were measured by integrating strain measuring strips as special tensile force sensors in the respective tape-shaped closing means.

FIG. 2 shows the result of further tensile stress measurements in the closing system of an incontinence diaper of this type for adults, wherein the average value and the maximum value of a plurality of measurements is shown in different practical situations. These different practical situations or wear situations for mobile patients are simulated i.a. by walking on a flat surface, climbing stairs, bending down, squatting, bending forward, lying down, moving back and forth, and standing up. The practical situations for immobile patients requiring care which are carried out by a nursing person while the patient is mostly in a prone position are simulated i.a. by bending one or both legs, raising the foot portion or upper body portion of a clinical bed, turning the test position to a 30°, 60°, 90° or 135° side position and turning back, changing the bedclothes while the patient remains prone. The respective blocks also show an average value and a maximum value for the upper (close to the hip) and lower (further removed from the hip) closing means, wherein a differentiation is additionally made between the above-mentioned physiological types (corpulent or slim). These tests also clearly show that the lower closing system disposed further removed from the hip is more loaded than the upper closing system closer to the hip.

Figure 3:
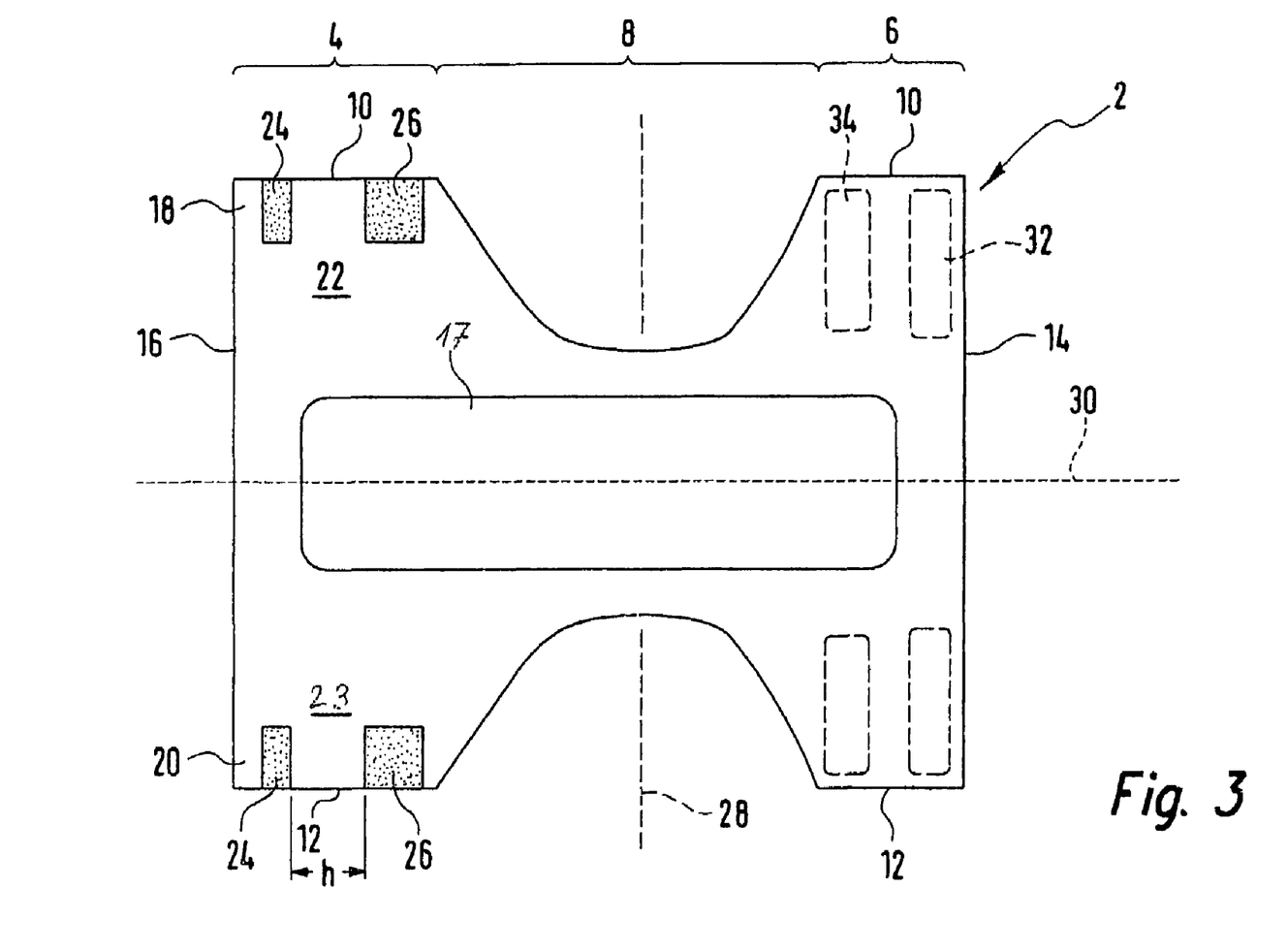
FIG. 3 shows a schematic plan view of an inventive incontinence diaper.

FIG. 3 schematically shows a plan view of an inventive incontinence diaper 2 with a rear area 4, a front area 6 and a center or crotch area 8 disposed therebetween, and longitudinal side edges 10, 12 of front area 6 and rear area 4 and hip edges 14, 16. A relatively narrow absorptive body 17 is also shown. A closing means 24 close to the hip and a closing means 26 further removed from the hip are disposed at a separation h of 105 mm In longitudinal edge sections 18, 20 of a respective side section 22, 23 of the rear area 4, which are preferably folded onto the visible side of the incontinence diaper 2. They can be unfolded to the outside such that they project over the respective longitudinal edge 10, 12 in a transverse direction 28 of the diaper 2. They may also be provided entirely within the side sections 22, 23. A longitudinal direction 30 of the incontinence diaper 2 extends perpendicular to this transverse direction 28.

The schematically shown closing means 24, 26 may be adhesive or mechanical, e.g. using hook/loop material. They may, in particular, be longitudinal sections of an endless strip or band material supplied in a longitudinal or transverse direction which is disposed in a "cut and place" method in the rear area 4 of the incontinence diaper 2.

In the present case, the indicated flat extension of the closing means 24, 26 may also represent its active adhesive area, i.e. a full-surface adhesive coating of the closing means, optionally with a non-coated grasping area. The area of this active adhesive area is thereby larger in the closing means 26 disposed further removed from the hip than in the closing means 24 disposed closer to the hip. In accordance with the invention, this produces, in particular with closing systems of the same kind, a stronger adhesive bond for the closing means 26 further removed from the hip which is released only under a higher releasing force than that for the closing means 24 closer to the hip. The adhesive bond is produced when the diaper 2 is worn by a user and the closing means 24, 26 are disposed or pressed onto associated impact areas 32, 34 in the front area 6 of the diaper. It has proven to be advantageous and simpler to design the respective impact areas 32, 34 in the same manner. They can be formed, in particular, from the upper side of a layered material of the diaper, e.g. of a foil sheet of the diaper, i.e. from polyethylene or polypropylene. They may also be hook or loop material disposed on a diaper side. Explicit reference is made to the above-mentioned statements about the design of the impact areas. If the closing means 24, 26 and the associated impact areas 32, 34 are designed to have the same function, the larger flat extension of the closing means 26 disposed further removed from the hip produces a stronger adhesive bond, as in the case shown. In other words, in accordance with the invention, at locations with high stresses, i.e. at the closing means 26 disposed further removed from the hip, the closing means and/or active adhesive areas are sized accordingly, whereas for the closing means disposed closer to the hip, closing means or active adhesive areas of smaller dimensions are sufficient. Raw material consumption can thereby be optimized in accordance with the requirements. The varying design of the adhesive bond in accordance with the invention can also be obtained or enhanced in another fashion than by providing closing means of different sizes or adhesive areas of different sizes for the closing means. It would e.g. also be feasible to provide the closing means disposed further removed from the hip with a different, stronger adhesive or to design the closing means and/or the associated impact area to produce a stronger adhesive bond.

A stronger adhesive bond between the closing means 26 disposed further removed from the hip and the associated impact areas 34 is preferably defined by determining the release forces, measured as shearing forces, which occur in a tensile force test. This is explained below with reference to the test set-up schematically shown in FIG. 4. This test method determines the bonding force between tape materials which simulate a closing means, and a test substrate which simulates an impact area. This composite adhesive force is determined using shearing stress in a tensile testing device 40 which is e.g. the schematically indicated tensile testing device 40 in accordance with EN ISO 527-1 (April 1996) with a fixed clamp 42 and a movable clamp 44 which serves to clamp the test substrate 46 and the closing means tape 48.

Figure 4:
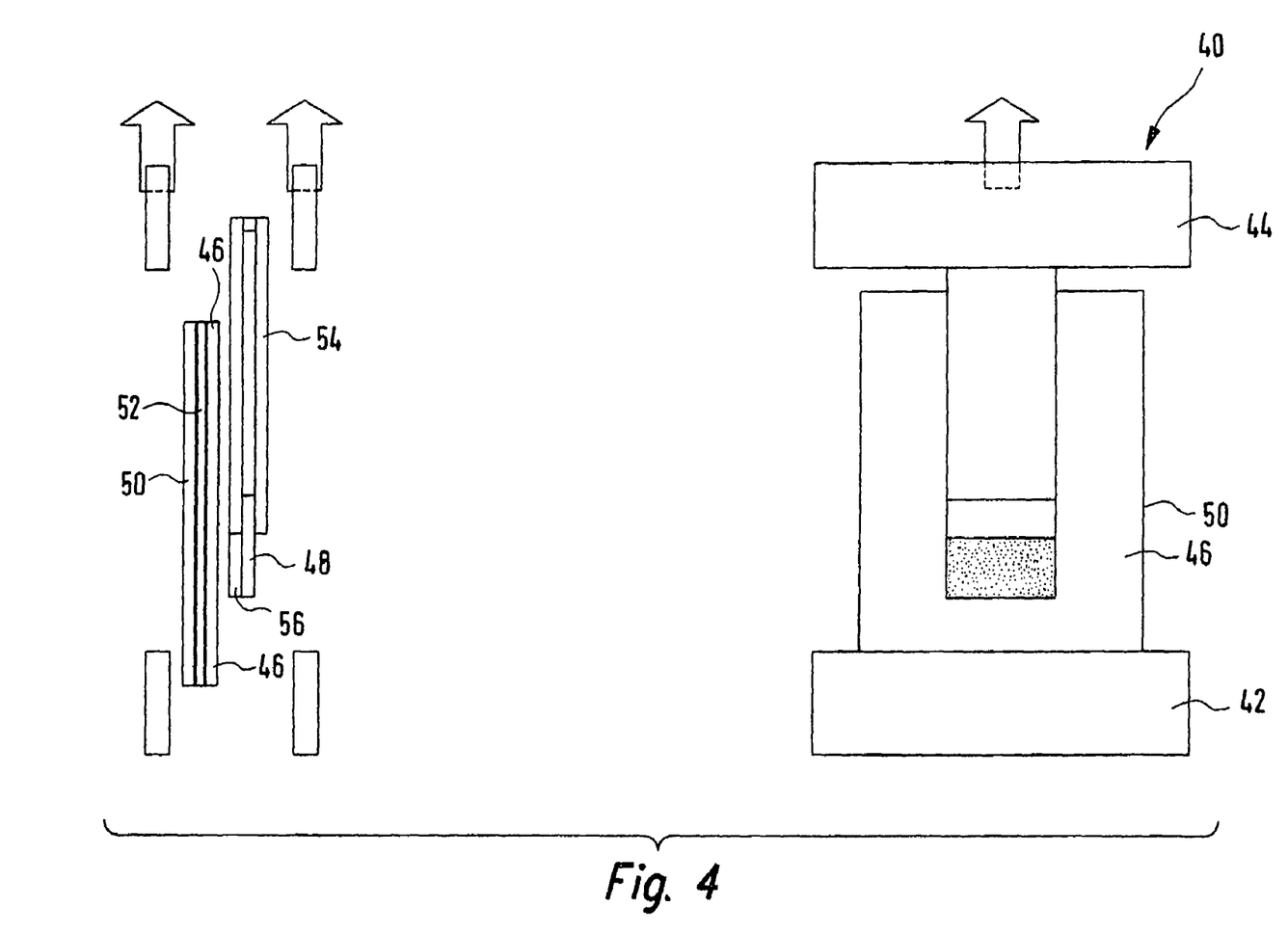
FIG. 4 shows the test set-up to determine the maximum releasing force.

To prepare the sample, the 55 mm wide test substrate 46 is disposed onto a 55 mm wide steel plate 50 using double-sided adhesive tape 52. The test substrate is a section of a conventional diaper back sheet foil, e.g. in the form of a polyethylene foil of a thickness of 21 μm, which is punched out transverse to the running direction.

The strip-shaped section of the closing means tape 48, which represents the closing means, is fixed between the legs of a U-shaped holding tape. The section 56, which is disposed in the upper plane, bears an adhesive coating with a surface density of 38 g/m²±4 g/m². A conventional adhesive containing an isoprene styrene copolymer is used. Referring to the figure, the tape 48 is pressed onto the test substrate 46 with an automatic rolling means using a pressure of 2.0 kg and a speed of 300 mm/min (a roller means of the type Viehoever RDG-002-291 can be used for this purpose).

The steel plate 50, adhesive tape 52 and test substrate 46 composite is then clamped over a relatively short clamping section into a clamp 42 of the tensile testing device and the U-shaped holding tape 54 is clamped into the other clamp 44. At a removing angle of substantially 0°, i.e. in the plane of the flat material composite, the movable clamp 44 is moved away from the stationary clamp with a speed of preferably 300 mm/min. The tensile force which acts between the clamps is thereby measured and rounded to two decimals in Newtons thereby stating the sample width, which may preferably be 29 mm. The measured values given below are each average values of six individual measurements, wherein differently dimensioned areas of the active adhesive bonding were selected which can be extracted from the following tables. The width of the tape 48 extending in a transverse direction 28 of the diaper is 29 mm for all measurements. The varying dimensions stated as lengths are oriented in a longitudinal direction 30 in the diaper. One can see from the right-hand column that the ratio of extension in the longitudinal direction 30 (length) of the closing means 24, 25 disposed close to the hip (upper tape) and further removed from the hip (lower tape) is between 1.2 and 2.0. This also applies for the ratio of the surface area of the active adhesive areas. One sees that the measured shearing forces which characterize the releasing forces, i.e. that force which rapidly releases the adhesive bond, have almost exactly the same ratio.

The method described therefore represents a possibility to define releasing forces as maximum shearing forces at a removal angle of 0° or to compare releasing forces of different closing means arrangements.

| Example# | length upper tape [mm] | length lower tape [mm] | ratio between lower tape length/upper tape length |
|---|---|---|---|
| 1 | 25 | 35 | 1.4 |
| 2 | 20 | 28 | 1.4 |
| 3 | 25 | 50 | 2.0 |
| 4 | 30 | 42 | 1.4 |
| 5 | 25 | 40 | 1.6 |
| 6 | 25 | 30 | 1.2 |

| Example# | shearing forces $F_{max}*$ up·tape[N] | shearing forces $F_{max}*$ low·tape[N] | ratio between shear forces $F_{max}*$ lower/upper tape |
| --- | --- | --- | --- |
| 1 | 48.2 | 66.5 | 1.4 |
| 2 | 39.9 | 55.0 | 1.4 |
| 3 | 48.2 | 96.1 | 2.0 |
| 4 | 57.3 | 79.0 | 1.4 |
| 5 | 48.2 | 75.2 | 1.6 |
| 6 | 48.2 | 57.3 | 1.2 |

*average value $F_{max}$ values from n = 6 measurements

I claim:

1. A disposable incontinence diaper for adults, the diaper having a front area, a rear area, and a center area disposed between the front and rear areas, the center area coming to rest in a crotch region of the user, the diaper comprising:
    first closing means disposed on side sections of the rear or front areas;
    first impact means disposed to cooperate with said first closing means during use of the diaper, said first closing means cooperating with said first impact means in an adhesive or mechanical fashion to close the diaper;
    second closing means disposed on side sections of the rear or front areas, said second closing means displaced in a longitudinal direction away from said first closing means to be further removed from a hip edge region of the diaper than said first closing means; and
    second impact means disposed to cooperate with said second closing means during use of the diaper, said second closing means cooperating with said second impact means in an adhesive or mechanical fashion to close the diaper, wherein said second closing means and said second impact means are structured and dimensioned such that an adhering bond between them when the diaper is closed is only released by a force which is larger than an adhering bonding force between said first closing means and said first impact means, wherein, as measured in a removal test as a maximum shearing force between said second closing means and said second impact means, a second force at which an adhering bond between said second closing means and said second impact means is released is between 45 N and 105 N and, as measured in a removal test as a maximum shearing force between said first closing means and said first impact means, a first force at which an adhering bond between said first closing means and said first impact means is released is between 38 N and 60 N.

2. The incontinence diaper of claim 1, wherein said first and said second closing means are disposed proximate longitudinal edge sections of the front or rear area.

3. The incontinence diaper of claim 1, wherein said second closing means has a larger active adhering area than said first closing means.

4. The incontinence diaper of claim 3, wherein said larger active adhering area of said second closing means is at least 1.2 times an active adhering area of said first closing means.

5. The incontinence diaper of claim 4, wherein said larger adhering area of said second holding means is between 1.2 and 2 times larger than said active adhering area of said first closing means.

6. The incontinence diaper of claim 1, wherein, in said longitudinal direction of the diaper, a dimension of an active adhering area of said second closing means is larger than a dimension of an active adhering area of said first closing means.

7. The incontinence diaper of claim 1, wherein, in said longitudinal direction of the diaper, a respective dimension of an active adhering area of said first and said second closing means substantially corresponds to a respective longitudinal dimension of said first and said second closing means.

8. The incontinence diaper of claim 1, wherein a longitudinal dimension of said second closing means is larger than a longitudinal dimension of said first closing means.

9. The incontinence diaper of claim 1, wherein a dimension of an active adhering area of said second closing means in a transverse direction of the diaper substantially corresponds to a dimension of an active adhering area of said first closing means in said transverse direction.

10. The incontinence diaper of claim 1, wherein, in said longitudinal direction of the diaper, said second closing means has a dimension of 24 to 55 mm and said first closing means has a dimension of 20 to 35 mm.

11. The incontinence diaper of claim 10, wherein, in said longitudinal direction of the diaper, said second closing means has a dimension of 30 to 40 mm and said first closing means has a dimension of 20 to 30 mm.

12. The incontinence diaper of claim 1, wherein, in said longitudinal direction, a separation between said first closing means and a hip edge of the diaper is 10 to 50 mm.

13. The incontinence diaper of claim 1, wherein, in said longitudinal direction, a separation between said first and said second closing means is 70 to 150 mm.

14. A disposable incontinence diaper for adults, the diaper having a front area, a rear area, and a center area disposed between the front and rear areas, the center area coming to rest in a crotch region of the user, the diaper comprising:
    first closing means disposed on side sections of the rear or front areas;
    first impact means disposed to cooperate with said first closing means during use of the diaper, said first closing means cooperating with said first impact means in an adhesive or mechanical fashion to close the diaper;
    second closing means disposed on side sections of the rear or front areas, said second closing means displaced in a longitudinal direction away from said first closing means to be further removed from a hip edge region of the diaper than said first closing means; and
    second impact means disposed to cooperate with said second closing means during use of the diaper, said second closing means cooperating with said second impact means in an adhesive or mechanical fashion to close the diaper, wherein said second closing means and said second impact means are structured and dimensioned such that an adhering bond between them when the diaper is closed is only released by a force which is larger than an adhering bonding force between said first closing means and said first impact means, wherein, as measured in a removal test as a maximum shearing force between said second closing means and said second impact means, a second force at which an adhering bond between said second closing means and said second impact means is released is between 55 N and 95 N and, as measured in a removal test as a maximum shearing force between said first closing means and said first impact means, a first force at which an adhering bond between said first closing means and said first impact means is released is between 40 N and 55 N.

15. A disposable incontinence diaper for adults, the diaper having a front area, a rear area, and a center area disposed between the front and rear areas, the center area coming to rest in a crotch region of the user, the diaper comprising:
first closing means disposed on side sections of the rear or front areas;
first impact means disposed to cooperate with said first closing means during use of the diaper, said first closing means cooperating with said first impact means in an adhesive or mechanical fashion to close the diaper;
second closing means disposed on side sections of the rear or front areas, said second closing means displaced in a longitudinal direction away from said first closing means to be further removed from a hip edge region of the diaper than said first closing means; and
second impact means disposed to cooperate with said second closing means during use of the diaper, said second closing means cooperating with said second impact means in an adhesive or mechanical fashion to close the diaper, wherein said second closing means and said second impact means are structured and dimensioned such that an adhering bond between them when the diaper is closed is only released by a force which is larger than an adhering bonding force between said first closing means and said first impact means, wherein, as measured in a removal test as a maximum shearing force between said second closing means and said second impact means, a second force at which an adhering band between said second closing means and said second impact means is released us between 55 N and 95 N and, as measured in a removal test as a maximum shearing force between said first closing means and said first impact means, a first force at which an adhering bond between said first closing means and said first impact means is released is between 40 N and 55 N, wherein said first and said second closing means are disposed proximate longitudinal edge sections of the rear area and a larger active adhering area of said second closing means is at least 1.2 times an active adhering area of said first closing means, wherein, in said longitudinal direction, a separation between said first and said second closing means is 70 to 150 mm.

* * * * *